(12) United States Patent
Kirchhofer

(10) Patent No.: US 7,789,858 B2
(45) Date of Patent: Sep. 7, 2010

(54) DEVICE FOR ADMINISTERING A FLUID PRODUCT

(75) Inventor: Fritz Kirchhofer, Sumiswald (CH)

(73) Assignee: TecPharma Licensing AG, Burgdorf (CH)

( * ) Notice: Subject to any disclaimer, the term of this patent is extended or adjusted under 35 U.S.C. 154(b) by 21 days.

(21) Appl. No.: 11/923,339

(22) Filed: Oct. 24, 2007

(65) Prior Publication Data
US 2008/0132840 A1 Jun. 5, 2008

Related U.S. Application Data

(63) Continuation of application No. PCT/CH2006/000221, filed on Apr. 24, 2006.

(30) Foreign Application Priority Data

Apr. 25, 2005 (CH) .................................... 0724/05

(51) Int. Cl.
*A61M 5/20* (2006.01)
*A61M 5/00* (2006.01)
*A61M 5/14* (2006.01)

(52) U.S. Cl. ...................... 604/135; 604/246; 604/256
(58) Field of Classification Search .................. 604/31, 604/65, 67, 131, 134, 135, 140, 141, 143, 604/214, 232, 890.1, 90, 150, 191, 246, 256
See application file for complete search history.

(56) References Cited

U.S. PATENT DOCUMENTS

| 1,869,443 | A | 8/1932 | Stocklin |
| 4,505,701 | A | 3/1985 | Navato et al. |
| 5,788,673 | A | 8/1998 | Young et al. |
| 2002/0161329 | A1 | 10/2002 | Gonnelli et al. |

FOREIGN PATENT DOCUMENTS

WO  WO 2004/089448 A1 * 10/2004

* cited by examiner

*Primary Examiner*—Nicholas D Lucchesi
*Assistant Examiner*—Victoria P Campbell
(74) *Attorney, Agent, or Firm*—Dorsey & Whitney LLP; David E. Bruhn, Esq.

(57) ABSTRACT

An administering device for a fluid product includes a product receptacle that accommodates the product to be administered, a fluid reservoir for a driving fluid, a driving means, a product chamber, and a fluid connection. The product receptacle includes an opening at a forward end and a product stopper at a rear end. The driving means acts upon the fluid reservoir, the pressure chamber adjoins the product stopper while the fluid connection is located between the fluid reservoir and the pressure chamber, and the driving means acts upon the fluid reservoir in such a way that the pressure chamber is impinged upon by pressure which affects the product stopper and the product is discharged from the product receptacle.

41 Claims, 4 Drawing Sheets

DEVICE FOR ADMINISTERING A FLUID PRODUCT

CROSS-REFERENCE TO RELATED APPLICATIONS

This application is a continuation of International Application No. PCT/CH2006/000221, filed 24 Apr. 2006, which claims the benefit of priority from Swiss Application No. 724/05, filed 25 Apr. 2005, the subject matter of both are hereby incorporated by reference in their entirety.

BACKGROUND

The present invention relates to devices for injecting, infusing, administering, delivering or dispensing substances, and to methods of making and using such devices. More particularly, the invention relates to a device for administering a fluid product, in particular a device for administering a fluid product at a continuous delivery rate.

For various diseases, such as for example diabetes, it can be necessary to continuously administer a particular amount of a fluid medicine to a patient. Various systems for this purpose are known, which enable the medicine to be supplied continuously over an extended period of time. The period of time of administration, the amount of the product administered within the period of time, the repetition rate of a number of consecutive administrations and possible extra deliveries can usually be set in such systems. Administering devices are known which can be connected to an external product container for a fluid medicine and, as soon as said container is empty, can be connected to the next container. Accordingly, such administering systems can be reused. Furthermore, implantable devices are also known which can be inserted into a patient's body tissue and are coupled to an external product container by means of a connector. Various possibilities exist for driving such systems, such as for example using gravity, various drive systems in the form of mechanical springs or hydraulic drives. In order to regulate the flow rate, the flow amount from the product container for the fluid medicine is usually limited at the outlet. Simple valves, clamps or programmable electronic devices can be used for this.

U.S. Pat. No. 5,788,673 discloses an infusion system in which a drive unit is combined with a conventional syringe. The syringe includes a product container that accommodates the fluid product, and a drive piston rod by which a product stopper within the product container can be advanced. The fluid product can be discharged from the syringe through an outlet opposite the product stopper. At the opening, the syringe also includes a valve for regulating the fluid flow. The drive unit comprises a chamber for a liquid medium, a second chamber which communicates with the first chamber, a piston and a valve system. A spring force can be exerted on the piston that conveys the liquid medium from the first chamber to the second chamber and back. The valve system controls the movement of the piston in the forward or backward direction and thus the discharge of the fluid product from the syringe.

The known systems for administering fluid medicines are generally designed to be reused. They therefore exhibit a complex construction comprising a large number of components and are therefore costly to manufacture. Furthermore, the patient or an assistant has to learn how to change the administering device from an empty product container to a new, full product container. If handled incorrectly, it is for example possible for an incorrect dosage to be administered to a patient.

SUMMARY

The present invention to provides a device for administering a fluid medicine, which is easy to handle, can be initiated in a few operating steps, ensures reliable functioning and ensures a continuous discharge at a constant medicine rate.

In addition, according to the invention, an administering device for continuously administering a fluid medicine, which is suitable for being used once, is provided.

The administering device of the present invention, according to certain embodiments, is configured to administer a fluid product, primarily a therapeutic medicine such as for example insulin. However, the administering device may also be used for administering other fluid products, which are to be administered into a body tissue. The administering device comprises a product container which accommodates the product to be administered and comprises an opening for discharging the product from the product container at its front, distal end, and a product stopper at its rear, proximal end. A typical ampoule, such as is used for injection syringes or pens for quickly administering small dosages and/or injection shots, may be used as the product container. The product stopper may be moved relative to the product container and seals the proximal end of the container in a fluid-proof seal.

According to various embodiments, the administering device also comprises a fluid reservoir for a drive fluid and a drive means that acts on the fluid reservoir. The drive fluid may be a non-compressible liquid. At least one of the fluid reservoir and the product container should be a non-compressible chamber; and in some implementations, the fluid reservoir and the product container are each formed by a non-compressible chamber. A non-compressible chamber may include solid, stable walls in a suitable geometric shape. The fluid reservoir includes a drive stopper, which transfers the action of the drive means onto the drive fluid within the fluid reservoir and charges the fluid reservoir with pressure. Various systems, including known systems, can be used as the drive means, such as for example mechanical springs, hydraulic drives or gas drives. A mechanical spring, for example a mechanical pressure spring, may be used as the drive means in the present invention.

A pressure chamber may be connected to the product stopper of the product container, according to some implementations. The pressure chamber may be formed by one or more walls of the product container, the product stopper and a closed end of the container. The closed end of the pressure chamber may be formed by a casing wall, such as by means of a seal. Accordingly, the pressure chamber may be at least partially or completely arranged within the product container. According to certain embodiments, the product container may be subdivided by the product stopper into a chamber for the product and the pressure chamber. A fluid connection is provided between the fluid reservoir and the pressure chamber, and the drive fluid may be conveyed out of the fluid reservoir, through the fluid connection, into the pressure chamber.

In accordance with the present invention, the drive means acts on the fluid reservoir in such a way that the pressure chamber is charged with pressure via the fluid connection, said pressure acting on the product stopper and thus discharging the product from the product container. Although for certain embodiments, a casing of the device forms a compartment for a product container, which is or can be accommodated in it, the casing, in other embodiments, may accommodate one or more or all of the components of the administering device in order to directly form the product container.

According to one embodiment of the present invention, the fluid connection exhibits a first, resting state in which it is closed, i.e. in which no drive fluid can flow from the fluid reservoir to the pressure chamber. A connecting means is provided in the administering device and moves the fluid connection from the first, closed, resting state to a second, open, administering state in which the fluid connection is open to the drive fluid. The connecting means therefore serves to connect the fluid reservoir containing the drive fluid to the pressure chamber connected to the product stopper of the product container. If, in the second, open state, the drive means then acts on the fluid reservoir or drive stopper of the fluid reservoir, the drive fluid is conveyed through the fluid connection.

According to certain embodiments, the drive means is biased in the administering device in the resting state, i.e. the drive means constantly acts on the fluid reservoir or drive stopper. The drive means may be held in the biased position by a holding and/or securing device. The holding device may include known locking systems in which, for example, the drive stopper of the drive means is held in place by a movable latch or stopper, for example, which may be removed or released by a push button or slider in order to release the locking system. In another embodiment, the holding device may be formed by the seal of the fluid connection, for example by means of the sealing membrane. The bias on the drive means may then be released by opening the fluid connection. In alternative embodiments, the drive means may only be tensed when the fluid connection is opened or after the fluid connection has been opened.

According to one embodiment, a casing is provided which accommodates the product container, the fluid reservoir, the pressure chamber and the fluid connection. In some implementations, a pre-assembled unit may be provided that includes the casing, the fluid reservoir, the pressure chamber and the fluid connection, and comprises a compartment into which the product container can be inserted when necessary, for example shortly before the required administration. Accordingly, in order to use the administering device in accordance with the invention, only the product container need be inserted into the casing compartment. When the product container is inserted into the casing, the connecting means may be activated, such that the fluid connection is moved from the resting state to the administrating state. If the drive means is already biased within the casing, the drive means may be triggered with the aid of the product container and the pressure chamber consequently charged with pressure. The pressure force begins to act on the drive stopper in such a way that the stopper is shifted relative to the fluid reservoir, and drive fluid flows from the fluid reservoir into the pressure chamber, wherein a pressure is built up in the pressure chamber which acts on the product stopper, and the fluid product is therefore discharged through the opening in the product container.

According to certain embodiments, the fluid connection comprises a sealing membrane for sealing it. The fluid connection may be moved from the closed state to the open state by penetrating the sealing membrane, and connecting means then exhibits a flow cross-section through which product can flow. For example, a tube-like hollow element, such as a hollow needle, conduit, capillary, or passage may serve as a connecting means and penetrate and/or pierce the sealing membrane of the fluid connection. Accordingly, the connecting means can form a part of the fluid connection. It is for example possible on the one hand for the fluid connection to be formed by a narrow capillary which feeds from the fluid reservoir, is conveyed within the casing towards the product container compartment, and is sealed with the sealing membrane at the end, which feeds into the compartment, and on the other for the fluid connection to be formed from the hollow needle of the connecting element. The pressure in the pressure chamber may be defined by dimensioning the fluid connection. The pressure in the pressure chamber is dependent on the size of the outlet area and/or the diameter of the fluid connection and on the length of the capillary. It is independent of the pressure of the drive element on the fluid reservoir or drive stopper. This implementation enables pressure fluctuations in the drive means to be equalized. In some implementations, the fluid connection may have a diameter of about 0.5 to about 3 mm. It is also possible to arrange the fluid connection within the casing in a looping, spiraling, meandering or labyrinthine manner. This enables the fluid connection path between the fluid space and the pressure chamber to be lengthened and the pressure in the pressure chamber to be regulated by selecting a particular fluid connection length.

In a particular embodiment, the connecting means forms a partial section of the fluid connection in the state in which the fluid reservoir is connected to the product reservoir. In another embodiment, the connecting means alone forms the fluid connection in the connected state. Alternatively, the hollow element, which penetrates the sealing membrane, may form the fluid connection. For example, the sealing membrane may form a wall of the fluid reservoir thus allowing the hollow element to form a fluid connection with the fluid in the reservoir once the hollow element penetrates the membrane.

The administering device of the present invention may be configured to be a single-use device. A user inserts the product container into the casing comprising the other components of the device, which in some embodiments, connects the pressure chamber to the fluid reservoir. Inserting may also simultaneously trigger administration. No further hand operations are necessary in order to initiate the device or regulate the administering amount. Once administration is complete, i.e. as soon as the product container is empty, the connection to the patient can be interrupted and the whole administering apparatus disposed of.

In alternative embodiments, the administering device may be reusable. If, for example, the drive means is only tensed or charged when the product container is inserted or after the product container has been inserted or by inserting the product container, the administering device may be repeatedly charged and used by again inserting a product container. The drive means can also be biased before a new product container is inserted.

According to some implementations, the connecting means is activated by the product stopper when the product container is inserted into the casing. As described, this can move the fluid connection from a closed state to an open state. It is, however, also simultaneously possible to form the connecting means in such a way that the product stopper within the product container is shifted in the distal direction of the product container when the container is inserted into the casing. The connecting means may advance the product stopper by a distance which allows the product container to be vented. This only requires a small movement by the product stopper within the product container, which may remove possible air pockets within the product container through the front opening of the product container, and the administering device may be directly connected to an administering conduit, which leads to the patient. The frictional force to overcome the snug fit of the product stopper in the product container is preferably greater than the force required to move the fluid connection from the closed state to the open state, i.e. to pierce the sealing membrane. When the product container is inserted, the membrane is then pierced first and the fluid connection between the fluid reservoir and the pressure chamber thus opened, and then the product stopper is distally shifted by a venting distance. The pressure building up in the pressure chamber immediately begins to advance the product stopper and thus administer the product.

In accordance with another aspect of the invention, a method is claimed, according to which, in a device for administering, and in some instances, for continuously administering, a fluid product, inserting a product container triggers the administration and/or a venting process for venting a product container.

DETAILED DESCRIPTION

Figure 1:
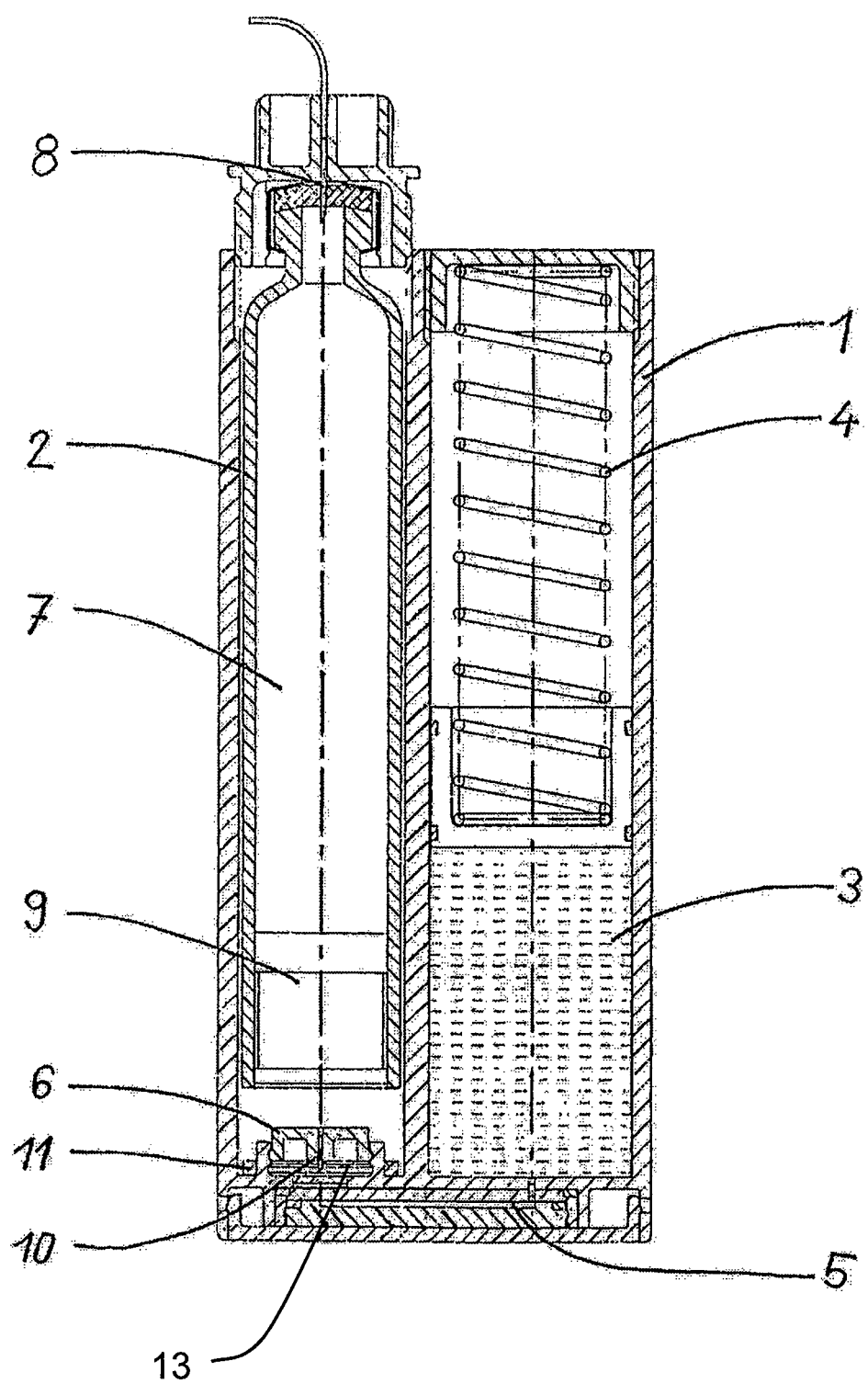
FIG. 1 depicts a first embodiment of an administering apparatus in accordance with the present invention, in a resting state.

FIG. 1 shows a first embodiment of an administering device in accordance with the present invention. The administering device comprises a casing (1) in which a product container in the form of an ampoule (2), a fluid reservoir (3), a drive means in the form of a spring (4), a fluid connection (5) and a connecting means (6) are accommodated. Water may be used as the drive fluid, the physical parameters of which are well known. However, it is also possible to use other fluids that differ in viscosity. The ampoule (2) is filled with the fluid product (7). Ampoule (2) comprises an opening (8) at its front, distal end and a product stopper (9) at its rear, proximal end. In FIG. 1, the ampoule (2) has not yet been completely inserted into the casing (1) and the administering device is in its resting state.

Figure 2:
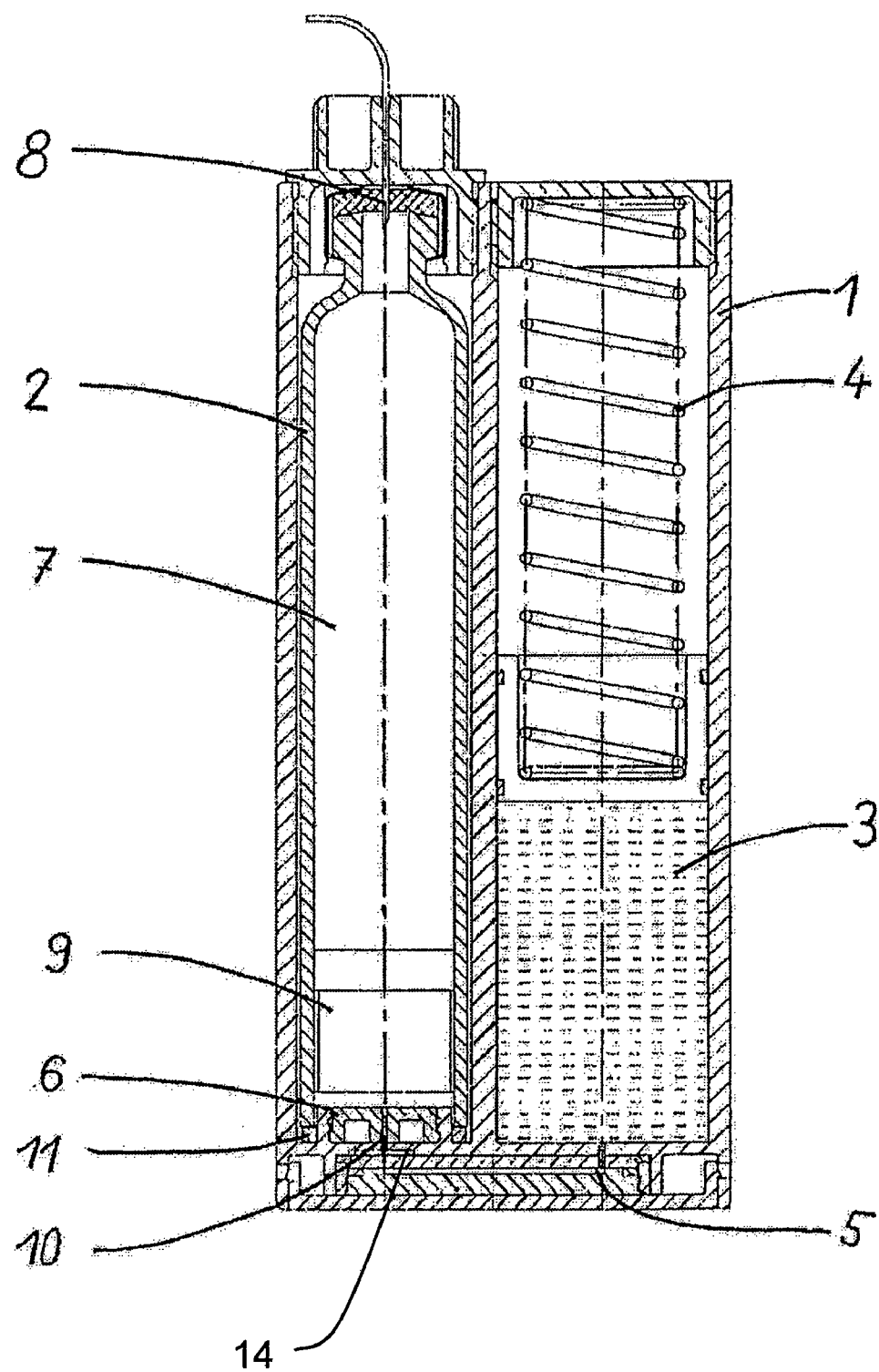
FIG. 2 depicts the administering device according to FIG. 1, in an administering state.
Figure 3:
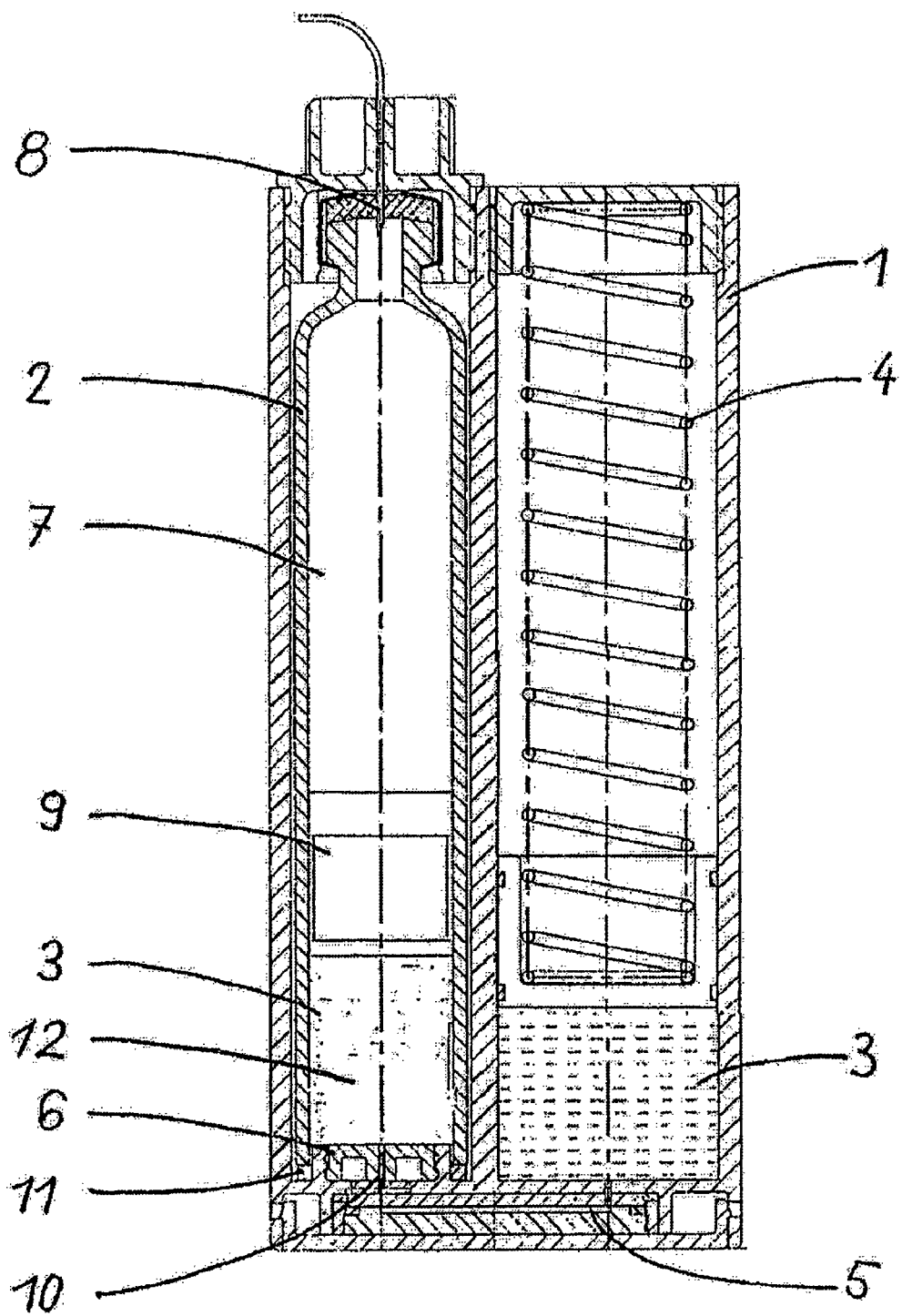
FIG. 3 depicts the administering device during administration.

In the embodiment in accordance with FIGS. 1 to 3, the ampoule (2) and the fluid reservoir (3) together with the spring (4) are arranged next to each other, offset in parallel, within the casing. The fluid connection (5) forms a transverse connection within the casing (1). This arrangement enables the overall length of the administering device to be kept small. The fluid connection (5) is spread over the area of the casing (1) in a number of loops (not shown).

The connecting means (6) is provided within the casing (1) as a movable element. The connecting means (6) can be moved along the longitudinal axis of the ampoule and is arranged between the ampoule (2) and the fluid connection (5) and comprises a hollow needle (10). The fluid connection (5) is permanently connected to the fluid reservoir (3) at one end and sealed by a sealing membrane (13) at the other end. The hollow needle (10) of the connecting element (6) is arranged opposite the sealing membrane (13) at an axially small distance. In addition, the connecting means (6) is provided centrally relative to the product stopper (9).

The system consisting of the spring (4), the fluid reservoir (3), the fluid connection (5) and the sealing membrane (13) forms a sealed fluid system in the resting state. In this embodiment, the spring (4) is already biased within the system. Even in the resting state, it therefore exerts a pressure on the fluid reservoir comprising the drive fluid. The sealing membrane (13) is therefore embodied such that it withstands this pressure.

In FIG. 2, the ampoule (2) has been completely inserted into the casing (1) of the administering device. When the ampoule (2) is completely inserted into the casing (1), the product stopper (9) comes to rest on the connecting means (6). If the ampoule (2) is inserted further, the product stopper (9) initially presses the connecting element (6) towards the sealing membrane (13) until the hollow needle (10) pierces the membrane and the connecting element (6) abuts a shift stopper (14), which may be formed by the casing or may be affixed to the casing. The connecting means (6) cannot then be shifted further in the direction of the longitudinal axis of the ampoule, relative to the casing. The ampoule (2) can, however, still be inserted further in the insertion direction, into the casing (1), wherein the product stopper (9), which abuts the connecting means (6), is shifted relative to the wall of the ampoule (2). This shift path of the product stopper (9) reduces the volume within the ampoule (2) for the fluid product, and the ampoule is vented and/or a small amount of the fluid product is discharged from the ampoule (2) through the opening (8). A small shift path of a few millimetres is sufficient for the venting process. The ampoule (2) is inserted into the casing (1) until it also abuts a shift stopper (14) within the casing, wherein the circumference of the proximal end of the ampoule (2) abuts a seal (11). In order to secure the ampoule (2) within the casing (1), a latching or locking mechanism can advantageously be provided.

The administering device is then in an administering state in which a fluid connection (5) is provided by piercing the sealing membrane (13) in the open state.

FIG. 3 shows the administering device in the administering state, after a certain product amount has been administered. The pressure chamber (12), which is formed by the wall of the ampoule (2), the product stopper (9), the connecting means (6) and the seal (11), can be seen in FIG. 3. Since the spring (4) is mounted, already biased, within the casing, opening the fluid connection (5) causes the drive fluid to flow from the fluid reservoir (3), through the fluid connection (5) through the hollow needle (10), into the pressure chamber (12). The flow amount through the fluid connection (5) depends on the diameter and length of the fluid connection (5). The pressure exerted on the product stopper (9) is therefore independent of variants in the pressure of the drive element, i.e. the spring (4). The discharge rate of the administering device can be defined by selecting the diameter and length of the fluid connection (5) and then remains constant throughout the administration of the fluid product (7) from the ampoule (2).

As soon as the product stopper (9) has reached the front, distal end of the ampoule (2), the ampoule is completely empty and the administering device can be disposed of.

Figure 4:
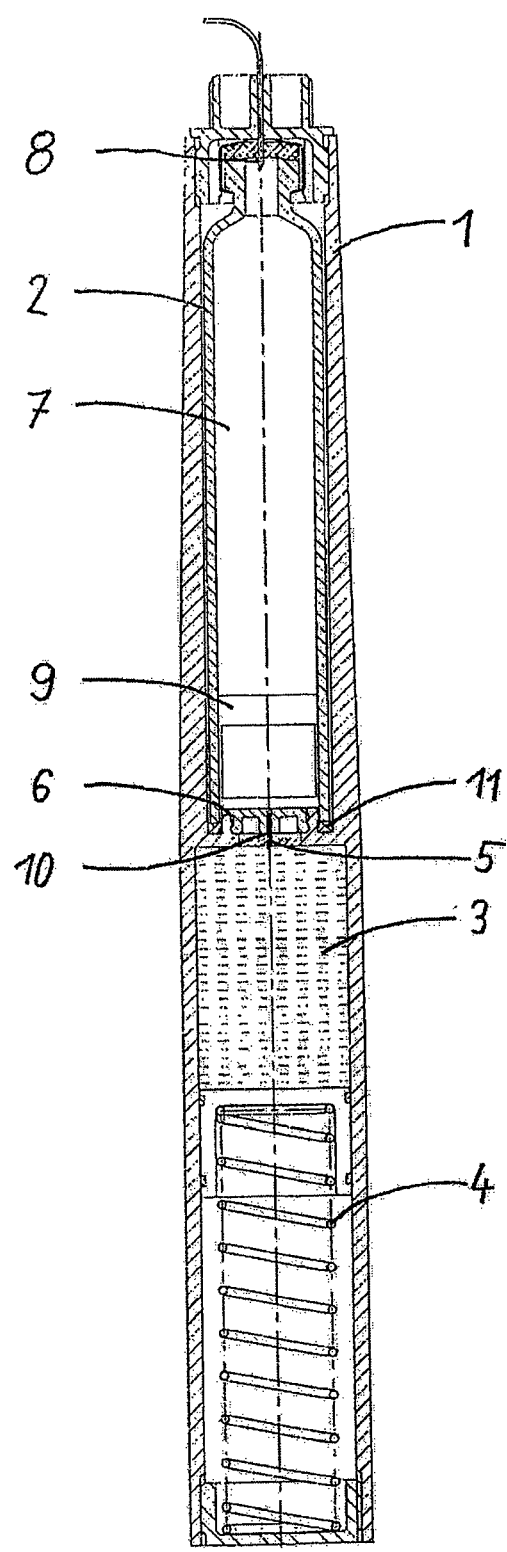
FIG. 4 depicts a second embodiment of an administering device in accordance with the present invention.

FIG. 4 shows another embodiment of the present invention, in which the ampoule (2), the fluid reservoir (3) and the drive spring (4) are arranged along the same axis within the casing (1). In this embodiment, the administering device exhibits a slim, elongated shape. Its mode of operation corresponds to the functioning of the embodiment from FIGS. 1 to 3.

In this second example embodiment, the connecting means (6), i.e. its hollow needle (10), alone forms the entire fluid connection (5) between the fluid reservoir (3) and the pressure chamber on the proximal side of the product stopper (9).

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for administering a fluid product, comprising:
    a product container configured to accommodate the fluid product to be administered, said product container comprising an opening at a front end and a product stopper movable relative to the product container at a rear end;
    a fluid reservoir for accommodating a drive fluid;
    a drive means operatively coupled to the fluid reservoir;
    a pressure chamber operatively coupled to the product stopper; and
    a connecting means for forming a fluid connection between the fluid reservoir and the pressure chamber, said connecting means comprising a first state and a second state, wherein the fluid connection is closed in the first state, and the fluid connection is opened in the second state such that the fluid connection is open to the drive fluid;
    wherein the connecting means forms a flow section of the fluid connection which exhibits a maximum flow resistance in the fluid connection;
    wherein, in the opened, second state, the drive means acts on the fluid reservoir in such a way that the pressure chamber is charged with pressure, which acts on the product stopper, and the product is discharged from the product container; and
    wherein when the product container is inserted into the device, the connecting means is activated in such a way that the fluid connection is moved to the second, open state.

2. The administering device according to claim 1, wherein the drive means is biased and/or held in a biased position.

3. The administering device according to claim 1, wherein the product container or the connecting means triggers the drive means.

4. The administering device according to claim 1, wherein the connecting means forms a part of the fluid connection.

5. The administering device according to claim 1, wherein the connecting means forms the fluid connection.

6. The administering device according to claim 1, wherein the connecting means comprises a tube-like hollow element with which a sealing membrane for sealing the fluid connection can be pierced.

7. The administering device according to claim 1, wherein the pressure chamber is formed by one or more walls of the product container and the product stopper together with the connecting means.

8. The administering device according to claim 1, wherein the fluid connection to the pressure chamber comprises a dimension, said dimension of the fluid connection defining the pressure in the pressure chamber.

9. The administering device according to claim 1, further comprising a casing, said casing configured as the fluid connection and fluid reservoir, and wherein the casing is configured to accommodate the drive means, the product container and the pressure chamber.

10. The administering device according to claim 1, further comprising a casing, said casing accommodating the drive means and each of the pressure chamber, the fluid connection, the product container and the fluid reservoir.

11. The administering device according to claim 10, wherein the product container is arranged next to the fluid reservoir and the drive means within the casing.

12. The administering device according to claim 10, wherein the product container, the fluid reservoir and the drive means are arranged along the same axis within the casing.

13. The administering device according to claim 1, wherein the drive means is a spring element.

14. The administering device according to claim 1, wherein the fluid connection is formed by a capillary having a diameter of 0.5 to 3 mm.

15. The administering device according to claim 1, wherein the fluid connection is formed in a meandering or looped shape.

16. A device for administering a fluid product, comprising:
    a product container configured to accommodate the fluid product to be administered, said product container comprising an opening at a front end and a product stopper movable relative to the product container at a rear end;
    a fluid reservoir for accommodating a drive fluid;
    a drive means operatively coupled to the fluid reservoir;
    a pressure chamber operatively coupled to the product stopper; and
    a connecting means for forming a fluid connection between the fluid reservoir and the pressure chamber, said connecting means comprising a first state and a second state, wherein the fluid connection is closed in the first state, and the fluid connection is opened in the second state such that the fluid connection is open to the drive fluid;
    wherein the connecting means forms a flow section of the fluid connection which exhibits a maximum flow resistance in the fluid connection;
    wherein, in the opened, second state, the drive means acts on the fluid reservoir in such a way that the pressure chamber is charged with pressure, which acts on the product stopper, and the product is discharged from the product container; and
    wherein when the product container is inserted into the device, the connecting means is activated by the product stopper.

17. The administering device according to claim 16, wherein the connecting means advances the product stopper by a distance that allows the product container to be vented.

18. The administering device according to claim 16, wherein the drive means is biased and/or held in a biased position.

19. The administering device according to claim 16, wherein the product container or the connecting means triggers the drive means.

20. The administering device according to claim 16, wherein the connecting means forms a part of the fluid connection.

21. The administering device according to claim 16, wherein the connecting means forms the fluid connection.

22. The administering device according to claim 16, wherein the connecting means comprises a tube-like hollow element with which a sealing membrane for sealing the fluid connection can be pierced.

23. The administering device according to claim 16, wherein the pressure chamber is formed by one or more walls of the product container and the product stopper together with the connecting means.

24. The administering device according to claim 16, wherein the fluid connection to the pressure chamber comprises a dimension, said dimension of the fluid connection defining the pressure in the pressure chamber.

25. The administering device according to claim 16, further comprising a casing, said casing configured as the fluid connection and fluid reservoir, and wherein the casing is configured to accommodate the drive means, the product container and the pressure chamber.

26. The administering device according to claim 16, further comprising a casing, said casing accommodating the drive means and each of the pressure chamber, the fluid connection, the product container and the fluid reservoir.

27. The administering device according to claim 26, wherein the product container is arranged next to the fluid reservoir and the drive means within the casing.

28. The administering device according to claim 26, wherein the product container, the fluid reservoir and the drive means are arranged along the same axis within the casing.

29. The administering device according to claim 16, wherein the drive means is a spring element.

30. The administering device according to claim 16, wherein the fluid connection is formed by a capillary having a diameter of 0.5 to 3 mm.

31. The administering device according to claim 16, wherein the fluid connection is formed in a meandering or looped shape.

32. A device for administering a fluid product, comprising:
a product container configured to accommodate the fluid product to be administered, said product container comprising an opening at a front end and a product stopper movable relative to the product container at a rear end;
a fluid reservoir for accommodating a drive fluid;
a drive means operatively coupled to the fluid reservoir;
a pressure chamber operatively coupled to the product stopper; and
a fluid connection between the fluid reservoir and the pressure chamber;
a sealing means, which seals the fluid connection;
a casing accommodating the product container, the fluid reservoir, the drive means, the pressure chamber and the fluid connection; and
a connecting means, which is accommodated in the casing in such a way that it can be moved from an initial position towards an activating position;
wherein the connecting means is arranged such that the product stopper can be coupled to the connecting means by inserting the product container, in order to move the connecting means to the activating position;
wherein the sealing means and the connecting means are arranged such that the connecting means is brought to bear on the sealing means by the movement into the activating position, in order to open the fluid connection; and
wherein the drive means acts on the fluid reservoir in such a way that the pressure chamber is charged with pressure which acts on the product stopper, and the product is discharged from the product container.

33. The administering device according to claim 32, wherein the connecting means comprises a bearing structure which is guided movably in the casing and a hollow element protrudes from the bearing structure and forms a section of the fluid connection in the activating position.

34. The administering device according to claim 32, wherein:
the casing forms a compartment comprising an opening; and
the product container can be inserted into the compartment through the opening, in the proximal direction;
wherein inserting the product container opens the fluid connection which is sealed before the product container is inserted.

35. The administering device according to claim 32, further comprising:
a compartment formed by the casing, said compartment comprising an opening through which the product container can be inserted into the compartment; and
a sealing element arranged in the compartment, said sealing arrangement configured to abut with the product container when it is inserted;
wherein the sealing element seals off a proximal end section of the inserted product container from the compartment.

36. The administering device according to claim 32, wherein the pressure chamber is formed by one or more walls of the product container and the product stopper together with the casing.

37. A device for administering a fluid product, comprising:
a product container configured to accommodate the fluid product to be administered, said product container comprising an opening at a front end and a product stopper movable relative to the product container at a rear end;
a fluid reservoir for accommodating a drive fluid;
a drive means operatively coupled to the fluid reservoir;
a pressure chamber operatively coupled to the product stopper; and
a connecting means for forming a fluid connection between the fluid reservoir and the pressure chamber, said connecting means comprising a first state and a second state, wherein the fluid connection is closed in the first state, and the fluid connection is opened in the second state such that the fluid connection is open to the drive fluid;
wherein when the product container is inserted into the casing, the connecting means is activated by the product stopper such that the connecting means is moved from the first state to the second state and advances the product stopper by a distance that allows the product container to be vented; and
wherein, upon venting the product container, the drive means acts on the fluid reservoir in such a way that the pressure chamber is charged with pressure which acts on the product stopper, and the product is discharged from the product container.

38. The administering device according to claim 37, further comprising a casing, said casing accommodating the drive means and each of the pressure chamber, the fluid connection, the product container and the fluid reservoir.

39. The administering device according to claim 37, wherein the pressure chamber is formed by one or more walls of the product container and the product stopper together with the connecting means.

40. The administering device according to claim 37, wherein the product container or the connecting means triggers the drive means.

41. The administering device according to claim 37, wherein the connecting means comprises a tube-like hollow element with which a sealing membrane for sealing the fluid connection can be pierced to move from the first state to the second state.

* * * * *